United States Patent
Russell

(10) Patent No.: US 10,398,729 B2
(45) Date of Patent: Sep. 3, 2019

(54) METHOD FOR TREATING ALZHEIMER'S DISEASE

(76) Inventor: Kenneth O. Russell, Austin, TX (US)

( * ) Notice: Subject to any disclaimer, the term of this patent is extended or adjusted under 35 U.S.C. 154(b) by 0 days.

(21) Appl. No.: 13/385,340

(22) Filed: Feb. 14, 2012

(65) Prior Publication Data

US 2013/0209580 A1    Aug. 15, 2013

(51) Int. Cl.
| | | |
|---|---|---|
| A61K 33/24 | (2019.01) | |
| A61K 31/59 | (2006.01) | |
| A61K 31/714 | (2006.01) | |
| A61K 33/04 | (2006.01) | |
| A61K 38/17 | (2006.01) | |
| A61K 36/82 | (2006.01) | |
| A61K 31/12 | (2006.01) | |
| A61K 31/133 | (2006.01) | |
| A61K 31/593 | (2006.01) | |
| A61K 31/7004 | (2006.01) | |
| A61K 35/20 | (2006.01) | |

(52) U.S. Cl.
CPC .............. *A61K 33/24* (2013.01); *A61K 31/12* (2013.01); *A61K 31/133* (2013.01); *A61K 31/59* (2013.01); *A61K 31/593* (2013.01); *A61K 31/7004* (2013.01); *A61K 31/714* (2013.01); *A61K 33/04* (2013.01); *A61K 35/20* (2013.01); *A61K 36/82* (2013.01); *A61K 38/17* (2013.01)

(58) Field of Classification Search
CPC ...... A61K 33/24; A61K 33/04; A61K 31/714; A61K 31/59; A61K 38/17; A61K 36/82; A61K 31/12; A61K 31/133; A61K 31/593; A61K 31/7004; A61K 35/20; A61K 2300/00
See application file for complete search history.

(56) References Cited

U.S. PATENT DOCUMENTS

| | | | | |
|---|---|---|---|---|
| 2001/0041695 A1* | 11/2001 | Koo | ..................... | A61K 31/205 514/168 |
| 2005/0074487 A1* | 4/2005 | Hsu | ..................... | A61K 8/0208 424/448 |
| 2006/0134228 A1* | 6/2006 | Kai | ..................... | A61K 31/28 424/655 |
| 2007/0184153 A1* | 8/2007 | Prasad | ..................... | A23L 33/15 426/73 |
| 2008/0269327 A1* | 10/2008 | Liu | ..................... | A61K 45/06 514/547 |
| 2008/0292607 A1* | 11/2008 | Mazzio | ..................... | A61K 31/19 424/94.1 |
| 2010/0021533 A1* | 1/2010 | Mazed | ..................... | A61K 36/02 424/450 |
| 2010/0234766 A1* | 9/2010 | Hermsmeyer | ..................... | A61K 9/0014 600/573 |

FOREIGN PATENT DOCUMENTS

WO    WO-2011023769 A1 *    3/2011    ........... A61K 36/064

OTHER PUBLICATIONS

Alzheimer's Disease Fact Sheet. [Retrieved on Apr. 17, 2013]. Retrieved from the internet <URL: http://www.nia.nih.gov/sites/default/files/alzheimers_disease_fact_sheet_0.pdf>.*
Bartzokis et al. Arch Gen Psychiatry, 2000, 57: 47-53. (Year: 2000).*
Patel et al. The Journal of Neuroscience, 2002, 22(15): 6578-6586. (Year: 2002).*

* cited by examiner

*Primary Examiner* — Doan T Phan
(74) *Attorney, Agent, or Firm* — Pham IP Group; Frank H. Pham

(57) ABSTRACT

A method of treating Alzheimer's Disease of users comprising daily use of a lotion, the components of which are disclosed, a daily supplementation with powdered whey protein and Vitamin D, and a mild exercise component.

2 Claims, No Drawings

METHOD FOR TREATING ALZHEIMER'S DISEASE

STATEMENT REGARDING FEDERALLY SPONSORED RESEARCH OR DEVELOPMENT

Not applicable.

BACKGROUND OF THE INVENTION

Field of the Invention

This invention relates to the field of personal health, and more specifically to a method of mitigating the debilitating effects of Alzheimer's Disease by a modification to the previous patent methods and products of Kenneth O. Russell regarding iron/chromium optimization.

Background of the Invention

Inventor Kenneth O. Russell has applied for U.S. Patents for several products related to health care, specifically for the uptake of nutrients into cells, for the reduction of blood glucose levels and for the general enhancement of cellular health (see above).

Alzheimer's Disease, the debilitating disease facing growing numbers of people in our aging population, has been called "Diabetes Type III" by many researchers. The inventor has found success in treating this disease by slightly modifying the methods claimed previously for treatment of Diabetes Type II. This Patent application discloses such methods.

Science.

The summary of currently known science of Alzheimer's Disease is well laid out in the scientific literature. However, the information, in its interactive totality, is not generally understood by even the medical community, let alone, by the general population. An attached addendum presents a summary of the science involved, with liberal references to published scientific journals in which all the pieces can be found. The preferred embodiment of this patent involves introducing some or all of the covered science prior to the introduction of products developed to reduce the knowledge into practice.

This patent disclosure has, as a central component, the chromium containing lotion disclosed in previous patent applications of the present inventor. The lotion so described uses as its base any commercially available skin lotion to which is added an aqueous solution containing chromium (III) which contains approximately 10 mg of chromium per ounce of lotion. The magnesium sulfate is a vasodilator which opens the pores of the skin slightly to facilitate absorption. In addition, the lotion contains an aqueous solution of magnesium sulfate with a concentration of approximately 1 g of magnesium sulfate per ounce of lotion. Finally vitamin B12 is added to the lotion in order to enhance the absorption of the chromium through the skin.

The protein powder of this invention increases serum levels of amino acids in the blood and has the effect of increasing ceruloplasmin which assists in the removal of iron from the cell. The increased muscle activity due to the exercise reduces catalytic iron which is liberated from the inactive muscles. This reduces the amount of iron that can be accumulated in the brain for its damaging influence in Alzheimer's and other pathologies.

The lotion described in this patent increases the immune response activity of muscle cells through the action of glutathione peroxidase. The lotion also increases protein synthesis for the formation of the ceruloplasmin and necessary for normal excretion of iron. Further beneficial effects of the lotion include lowering the levels of insulin related triglyceride formation and reducing cholesterol accumulation. Finally, the lotion enhances insulin signaling influence on amino acid absorption with its downstream benefit of improved cognition.

BRIEF SUMMARY OF SOME OF THE PREFERRED EMBODIMENTS

This patent application discloses a simple treatment of Alzheimer's disease consisting of three steps:

First, a lotion containing Chromium (III), Magnesium Sulfate and Vitamin $B_{12}$ (as described above) is applied to the skin regularly. The amount of Chromium in the lotion is calculated to deliver between 200-1,000 micro-grams of Chromium (III) for each application Second, a supplement regimen consisting of approximately 20-40 grams of powdered whey protein stirred into any liquid and drunk along with a large dosage of Vitamin $D_3$. The amount of Vitamin D supplementation can vary between about 5,000-20,000 International Units (IU) of Vitamin D per dose.

Finally, the treatment also includes an exercise component, wherein the patient engages in any modest exertion which will elevate his/her heart rate from a slight elevation up to about 70% of maximum and maintained at that rate for 10-30 min.

The most effective treatment is when the exercise component immediately follows the application of the lotion and the consumption of the supplements. Further, it is recommended that the treatment be done regularly, as often as twice daily.

Without being limited by theory, the business method disclosed herein may result in the individual users having decreased fasting blood sugar, increased sleep quality, reduced depression, increased food satiety, enhanced stamina, shorter recovery times, reduced carbohydrate craving, increased weight loss, increased muscle mass and energy levels, reduced fatigue or increased athletic performance.

Although the present invention and its advantages have been described in detail, it should be understood that various changes, substitutions and alterations may be made herein without departing from the spirit and scope of the invention as defined by any claims.

A further embodiment of this patent calls for the use of iron chelation therapy to assist in the removal of iron from the body. There are several modern drug therapies being used for iron chelation, however, this patent disclosure only makes use of commonly available chemicals. The most effective way to remove iron from the cells is by ceruloplasmin synthesized from the protein supplements as assisted by the chromium in the lotion. Other effective to celation therapies include curcumin (found in the spice curry), dimethyl amino ethanol (DMAE), inositol and green tea extract.

DETAILED DESCRIPTION OF THE PREFERRED EMBODIMENT

In the preferred embodiment of this convention, a person would first ingest a drink into which whey protein powder had been stirred. The liquid into which the protein powder is added is not critical. However, for best effect, it should contain very few carbohydrates. In addition to the protein drink, the person would also ingest vitamin D tablets containing between 5,000-20,000 International Units. (IU) of vitamin D. Next, the person would topically apply the lotion as described above. The typical application of the lotion would entirely cover the arms and legs of the user, however more extensive coverage on the torso is also efficacious. Finally, the person would engage in physical activity designed to elevate his pulse rate to at least 60% of maximum for at least 10 minutes.

Alzheimer's Facts

Iron

Iron related Reactive Oxygen Species (ROS) is responsible for early neuronal cell death. It is now established that oxidative stress is one of the earliest, if not the earliest, change that occurs in the pathogenesis of Alzheimer's disease (AD). Consistent with this, mild cognitive impairment (MCI), the clinical precursor of AD, is also characterized by elevations in oxidative stress. Since such stress does not-operate in vacuo, in this study we sought to determine whether redox-active iron, a potent source of free radicals, was elevated in MCI and preclinical AD as compared to cognitively-intact age-matched control patients. Increased iron was found at the highest levels both in the cortex and cerebellum from the pre-clinical AD/MCI cases. Interestingly, glial accumulations of redox-active iron in the cerebellum were also evident in preclinical AD patients and tend to increase as patients became progressively cognitively impaired. Our findings suggests that an imbalance in iron homeostasis is a precursor to the neurodegenerative processes leading to AD and that iron imbalance is not necessarily unique to affected regions. In fact, an understanding of iron deposition in other regions of the brain may provide insights into neuroprotective strategies. Iron deposition at the preclinical stage of AD may be useful as a diagnostic tool, using iron imaging methods, as well as a potential therapeutic target, through metal ion chelators.

Amino acids for new cell growth and antioxidant function. Whey protein concentrate consumption in adults is associated with a significant increase in protein synthesis, with no change in protein catabolism.[2]

Iron accumulates as a function of age in several tissues in vivo and is associated with the pathology of numerous age-related diseases. The molecular basis of this change may be due to a loss of iron homeostasis at the cellular level. Total iron content increases exponentially during cellular senescence. Iron accumulation occurs during normal cellular senescence in vitro. This accumulation of iron may contribute to the increased oxidative stress and cellular dysfunction seen in senescent cells.[3]

A recent study examined the effects of iron overload on telomere length and telomerase activity. Mean telomere lengths were similar in iron-loaded and control livers. However, telomerase activity was increased 3-fold by iron loading. Telomeres are repeated sequences $(TTAGGG_n)$ at the ends of chromosomes that are incompletely copied when DNA is replicated during mitosis. In cells lacking a mechanism to restore telomeric sequences, telomeres therefore shorten progressively with each round of cell division. When telomeres reach a threshold length, cells withdraw from the cell cycle and acquire a senescent phenotype. Thus, the inexorable shortening of telomeres with each round of cell division is regarded as a "mitotic clock" that records the number of antecedent cell divisions and signals the onset of phenotypic alterations associated with aging. A substantial body of data indicates that telomere attrition is modulated by oxidant-antioxidant balance. The finding that telomere lengths were not dramatically altered by iron loading suggested that telomerase activity might be increased in the iron leaded livers.[4]

Quiong, et al adopted flow cytometry and fluorescence in situ hybridization to investigate the impact of different elements on cellular apoptosis and telomere lengths of human hepatocytes L-02 and hepatoma cells SMMC-7721. Regarding hepatoma cells SMMC-7721, 20.0 µmol/L chromic chloride, remarkably extended the telomere lengths. The results revealed differential effects of trace elements on the life-span of human hepatocytes and hepatoma cell lines, which suggested further research on somatic hepatocytes and hepatoma in vivo.[5]

Amyloid Beta (Aβ or Abeta) Plaque

Amyloid beta is a peptide of 39-43 amino acids that appears to be the main constituent of amyloid plaques in the brains of Alzheimer's disease patients. The "amyloid hypothesis", that the plaques are responsible for the pathology of Alzheimer's disease, is accepted by the majority of Alzheimer's researchers. Aβ is formed after sequential cleavage of the amyloid precursor protein (APP), a transmembrane glycoprotein of undetermined function. Mutations in APP associated with early-onset Alzheimer's have been noted to increase the relative production of $A\beta_{42}$. It may be caused by uploading of inappropriately higher levels of large neutral amino acids and reduced levels of tryptophan Abeta plaque, may reduce prevailing neuronal cell mortality work by Naslund et al showing increases in brain Aβ with early cognitive dysfunction and even prior to plaques and tangles, support the proposal that soluble Aβ and not plaques may initiate AD pathology.[6]

Current thinking is that it is necessary to block amyloid formation or get rid of amyloid plaque accumulations and if you start treatment before the disease is well under way, you might have a chance to alter its course. Current drug therapy is testing whether actual removal of Abeta plaque will improve memory of Alzheimer's patients. However, a series of recent trials has had disappointingly negative results that raise questions about drug development strategies.[7]

UCLA professor of psychiatry George Bartzokis argues that However, amyloid beta may actually develop as a result of the natural process of the repair and maintenance of myelin. He contends that the breakdown that leads to Alzheimer's and other age-related brain diseases, such as Parkinson's, may begin much earlier, before the formation of the protein deposits that are used to define these diseases.

Most drugs being developed for Alzheimer's are targeting amyloid beta, but little if any clinical improvement is being seen. This is, according to Bartzokis, "similar to cleaning up a house that's been flooded by water but never repairing the actual pipe that created the flood. "For drug development then, the targets should be much further upstream, earlier in the process before the AB plaques even develop," he said.

Instead of focusing on reducing amyloid, beta, Bartzokis argues, the myelin model suggests entirely different approaches to treatment and prevention of Alzheimer's disease that precede plaque formation. With modern brain imaging technology, clinicians could track the dynamic changes taking place in the brain and intercede well before any signs of Alzheimer's are seen.[8]

Carbohydrates and Obesity

In the past few years, it has emerged that being overweight in middle age is linked to an increased risk of Alzheimer's Disease and other forms of dementia. Two studies strengthen this association: the first, shows that abdominal fat is linked to reduced brain volume in otherwise healthy middle-aged adults.[9] The second shows that this reduction is associated with a common variant of an obesity-related gene.[10]

Individuals with mild cognitive impairment who take huge doses of B vitamins everyday may reduce the rate at which their brains shrink by 50%, resulting in a much slower progression toward dementia, and eventually Alzheimer's disease. People short on the nutrient were 6 times more likely than individuals with normal levels to experience brain shrinkage, which is strongly linked to dementia.[11]

Eating a diet rich in a certain type of omega-3 fatty acid may slow or even prevent Alzheimer's disease.[12]

MIT brain researchers have developed a "cocktail" of dietary supplements (omega-3 fatty acids, uridine and choline—are all needed by brain neurons to make phospholipids, the primary component of cell membranes), now in human clinical trials, that holds promise for the treatment of Alzheimer's disease.[13]

Cole, et al, report that the omega-3 fatty acid docosahexaenoic acid (DHA) found in fish oil increases the production of LR11, a protein that is found at reduced levels in Alzheimer's patients and which is known to destroy the protein that forms the beta amyloid plaques associated with the disease. The plaques are thought to be toxic to neurons in the brain, leading to Alzheimer's. Since having high levels of LR11 prevents the toxic plaques from being made, low levels in patients are believed to be a factor in causing the disease.[14]

researchers have found that insulin levels affect the brain's dopamine systems.[15]

Unfit children have lower cognition expression at 9-10
Carbohydrate breakfasts increase cognition
Senior mice and senior humans exhaust hippocampus glucose quickly
Hippocampus glucose improves performance in mice maze activity The pathology of Alzheimer's disease (AD) is characterized by cerebral atrophy in frontal, temporal, and parietal regions, with senile plaques, dystrophic neurites, and neurofibrillar tangles within defined areas of the brain. Another characteristic of AD is regional hypometabolism in the brain. This decline in cerebral glucose metabolism occurs before pathology and symptoms manifest, continues as symptoms progress, and is more severe than that of normal aging. Ketone bodies are an efficient alternative fuel for cells that are unable to metabolize glucose or are 'starved' of glucose. AC-1202 is designed to elevate serum ketone levels safely. We previously showed that treatment with AC-1202 in patients with mild-to-moderate AD improves memory and cognition. Treatment outcomes were influenced by apolipoprotein E genotype status. These data suggest that AC-1202 may be an effective treatment for cognitive dysfunction by providing an alternative substrate for use by glucose-compromised neurons.[16]

Normally, the brain's fuel is glucose, but during fasting it increasingly relies on ketones (β-hydroxybutyrate, acetoacetate, and acetone) produced in liver mitochondria from fatty acid β-oxidation. Although moderately raised blood ketones produced on a very high fat ketogenic diet have important clinical effects on the brain, including reducing seizures, ketone metabolism by the brain is still poorly understood. The aim of the present work was to assess brain uptake of carbon-11-labeled acetoacetate ($^{11}$C-acetoacetate) by positron emission tomography (PET) imaging in the intact, living rat. To vary plasma ketones, we used three dietary conditions: high carbohydrate control diet (low plasma ketones), fat-rich ketogenic diet (raised plasma ketones), and 48-h fasting (raised plasma ketones). $^{11}$C-acetoacetate metabolism was measured in the brain, heart, and tissue in the mouth area. Using $^{11}$C-acetoacetate and small animal PET imaging, we have noninvasively quantified an approximately seven- to eightfold enhanced brain uptake of ketones on a ketogenic diet or during fasting. This opens up an opportunity to study brain ketone metabolism in humans.[17]

One of the main features of Alzheimer's disease (AD) is the severe reduction of the cerebral metabolic rate for glucose (CMRglc). In vivo imaging using positron emission tomography With 2-[$^{18}$F]fluoro-2-deoxy-D-glucose (FDG-PET) demonstrates consistent and progressive CMRglc reductions in AD patients, the extent and topography of which correlate with symptom severity. Increasing evidence suggests that CMRglc reductions occur at the preclinical stages of AD. CMRglc reductions were observed on FDG-PET before the onset of disease in several groups of at-risk individuals, including patients with mild cognitive impairment (MCI), often a prodrome to AD; presymptomatic individuals carrying mutations responsible for early-onset familial AD; cognitively normal elderly individuals followed for several years until they declined to MCI and eventually to AD; normal, middle-aged individuals who expressed subjective memory complaints and were carriers of the apolipoprotein E epsilon-4 allele, a strong genetic risk factor for late-onset AD. However, the causes of the early metabolic dysfunction forerunning the onset of AD are not known. An increasing body of evidence indicates a deficient or altered energy metabolism that could change the overall oxidative microenvironment for neurons during the pathogenesis and progression of AD, leading to alterations in mitochondrial enzymes and in glucose metabolism in AD brain tissue. The present paper reviews findings that implicate hypometabolism and oxidative stress as crucial players in the initiation and progression of synaptic pathology in AD.[18]

The Relationship Between Chromium and Alzheimer's Disease

Providing supplemental chromium picolinate to elderly adults with early memory decline can improve cognitive performance and brain function.[19] Insulin resistance is implicated in the pathophysiological changes associated with Alzheimer's disease, and pharmaceutical treatments that overcome insulin resistance improve memory function in subjects with mild cognitive impairment (MCI) and early Alzheimer's disease.[20] An alternate theory of Alzheimer's Disease and diabetes holds that Alzheimer's Disease is not caused by the increase in insulin from Type II diabetes. Rather, there is improper insulin handling occurring directly in the brain (probably from inadequate chromium). People are calling this 'Type III Diabetes'. Previous studies have suggested an acutely improving effect of insulin on memory function. Subjects after insulin reported signs of enhanced mood, such as reduced anger and enhanced self-confidence. Results indicate a direct action of prolonged intranasal administration of insulin on brain functions, improving memory and mood in the absence of systemic side effects.[21]

Conditions in which glucose metabolism is impaired due to insulin resistance are associated with memory impairment. It was hypothesized that supplemental chromium (Cr) may alleviate insulin resistance in type 2 diabetes and consequently improve memory acquisition, depending upon its source and level. High-fat diet caused a 32% reduction in expressions of glucose transporters 1 and 3 (GLUTs) in brain tissue and a 27% reduction in mean percentage time spent in the target quadrant and a 38% increase in spatial memory acquisition phase (SMAP) compared with ND. Compared with supplemental Cr as CrAc, CrGly was more effective to ameliorate response variables (i.e., restoration of tissue Cr concentration, enhancement of cerebral GLUTs expressions, and reduction of the glucose/insulin ratio and SMAP) in a dose-response manner, especially in rats fed HFD. Supplemental Cr as CrGly may have therapeutic potential to enhance insulin action and alleviate memory acquisition in a dose-dependent manner, through restoring tissue Cr reserve and enhancing cerebral GLUTs expressions.[22]

Chromium's Role on Transport of Iron into Brain

Chromium supplementation will decrease the ratios\amounts of iron on transferrin molecules. Each activation of the insulin receptor culminates with the activation of a transferrin receptor on the cell membrane. When the transferrin receptor draws in a transferrin molecule, iron and/or chromium is released into the cell contents. When four chromic ions secure the intracellular base unit of the insulin receptor, no phosphatase cleavage will interrupt the ongoing insulin signaling enterprise (an indefinite extension of the signaling may survive without any additional activities of the transferrin receptor influence on iron loading). in the absence of the four chromic ions securing the insulin base unit, many successive activations of the transferrin receptors will multiply the amount of iron and chromium that will be loaded over a given period or feeding event, chromium is ejected from the cell after each phosphatase cleavage interruption, but iron is never ejected.

Chromium's Role on Transport of Tryptophan into Brain

Chromium helps to promote conversion of tryptophan to serotonin by facilitating absorption into muscle tissue of the amino acids that compete with tryptophan for access to the brain.

Iron and Alzheimer's

*Targeting multiple Alzheimer's disease etiologies with multimodal neuroprotective and neurorestorative iron chelators.* Tamar Amit, Yael Avramovich-Tirosh, Moussa B. H. Youdim[1] and Silvia Mandel *The FASEB Journal.* 2008; 22:1296-1305. The Federation of American Societies for Experimental Biology An imbalance in iron homeostasis is a precursor to the neurodegenerative processes leading to AD and that iron imbalance is not necessarily unique to affected regions. In fact, an understanding of iron deposition in other regions of the brain may provide insights into neuroprotective strategies. Iron deposition at the preclinical stage of AD may be useful as a diagnostic tool, using iron imaging methods, as well as a potential therapeutic target, through metal ion chelators.[23]

Research findings indicate that there are alterations of iron homeostasis in Alzheimer's Disease, and this is supported by the recent demonstration of elevated serum levels of the iron binding protein p97 in patients with AD. Furthermore, the presence of redox-available iron in association with pathological lesions, coupled with the increasing number of reports implicating oxidative stress, strongly support the key rote that oxidative damage plays in the pathogenesis of AD.[24]

Iron accumulates as a function of age in several tissues in vivo and is associated with the pathology of numerous age-related diseases. The molecular basis of this change may be due to a loss of iron homeostasis at the cellular level. Therefore, changes in iron content in primary human fibroblast cells (IMR-90) were studied in vitro as a model of cellular senescence. Total iron content increased exponentially during cellular senescence, resulting in 10-fold higher levels of iron compared with young cells. Low-dose hydrogen peroxide ($H_2O_2$) induced early senescence in IMR-90s and concomitantly accelerated iron accumulation. Furthermore, senescence-related and $H_2O_2$-stimulated iron accumulation was attenuated by N-tert-butylhydroxylamine (NtBHA), a mitochondrial antioxidant that delays senescence in vitro. However, SV40-transformed, immortalized IMR-90s showed no time-dependent changes in metal content in culture or when treated with $H_2O_2$ and/or NtBHA. These data indicate that iron accumulation occurs during normal cellular senescence in vitro. This accumulation of iron may contribute to the increased oxidative stress and cellular dysfunction seen in senescent cells.[25]

Iron circulating in transferrin in the blood cannot directly cross the blood brain barrier (BBB). There are several pathways that can transfer iron across the BBB. The first and probably most common is through transferrin receptors on brain endothelial cells, which bind iron circulating in the form of transferrin. The transferrin receptor-bound complex then enters the brain by endocytosis. Several other transporter systems may also deliver iron across the BBB, such as the divalent metal transporter and the lactoferrin receptor.

In addition, these pathways, especially the transferrin-receptor mediated pathway, are the main avenues for iron transport within the CNS (i.e., into various cell types of the brain). The amount of iron taken up and stored by the cells is a function of the abundance of the transferrin receptor and its ligand. Ferritin is the most common iron-storage protein in the brain. Another sequestrant of iron found in high concentrations in the substantia nigra and locus ceruleus is neuromelanin. There is evidence to suggest that neuromelanin acts to reduce potentially toxic iron by chelating iron found in the cytosol of neurons. Finally, after the brain uses the iron it has stored, the iron must leave the cell, and the copper-associated protein ceruloplasmin may facilitate cellular release of iron.

Iron deposition is gaining increased recognition as a putative factor in the pathogenesis of AD. Animal models, pathologic, studies, and MRI have linked iron to AD. Animal studies suggest that excessive iron contributes to oxidative stress and neuronal injury through the production of hydroxyl free radicals. Animal models also suggest that increases in iron may either worsen the course or increase the risk of developing AD. It is also established from postmortem pathology studies that iron deposition occurs in neurons, neurofibrillary tangles and plaques of patients with AD. Progress has been made in identifying the role of iron in AD using experimental in vivo and in vitro models. For example, iron exacerbates amyloid-induced neuronal injury in human neuroblastoma cell line M17 and also enhances aggregation of beta amyloid proteins in vitro. Further, iron augments beta amyloid neurotoxicity. Finally, genetics Studies have also indicated that mutations of genes involved in iron management can increase the risk of AD. Mutations in the transferrin and hereditary hemochromatosis (HFE) gene lead to deranged iron metabolism and confer a risk for development of AD.[26,27]

Dementia can be caused by severe niacin insufficiency, but it was unknown whether variation in intake of niacin in the usual diet is linked to neurodegenerative decline. Morris, et al examined whether dietary intake of niacin was associated with incident Alzheimer's disease (AD) and cognitive decline in a large, prospective study. The found that energy adjusted niacin intake had a protective effect on development of AD and cognitive decline.[28]

Vitamin D

Previous studies revealed some comorbidity of Alzheimer's disease and osteoporosis not only for advanced disease, but also for the incipient conditions cognitive decline and decline of bone mineral density. Luckhaus et at found that there is a significant correlation between concentrations of biochemical osteoporosis markers in blood plasma of subjects with mild cognitive impairment and mild Alzheimer's disease compared to subjects with primary osteoporosis and age-matched cognitively normal controls. These results point to increased bone catabolism and concomitant remodelling/anabolism unrelated to vitamin D state in mild Alzheimer's disease, but not, in mild cognitive impairment. This corroborates previous findings of comorbidity of Alzheimer's disease with osteoporosis in the early disease course at the level of biochemical blood markers.[29]

Patients with Alzheimer's disease (AD) suffer from brain amyloidosis related to defective clearance of amyloid-beta (Abeta) by the innate immune system. Missouli et al studied immune stimulation of macrophages by vitamin D3 (1,25D3) in combination with curcuminoids. They found that 1,25D3 strongly stimulated Abeta phagocytosis and clearance while protecting against apoptosis.[30]

Vitamin D insufficiency and deficiency was associated with all-cause dementia, Alzheimer disease, stroke (with and without dementia symptoms), and MRI indicators of cerebrovascular disease. These findings suggest a potential vasculoprotective role of vitamin D.[31]

Oudshoom found an association between Mini Mental State Exam (MMSE) test scores and serum 25-hydroxyvitamin D(3) levels. Vitamin-D-sufficient patients had significantly higher MMSE scores as compared to vitamin-D-insufficient ones. No association was found with the other serum vitamin levels.[32] In a cross-section of older adults, Wilkins found that vitamin D deficiency was associated with low mood and with impairment on two of four measures of cognitive performance.[33]

Vitamin D supplementation has also been associated with protecting the length of telomeres. In a study by researchers from the London School of Medicine, serum vitamin D concentrations were measured in 2,160 women, aged 18-79 years (mean age: 49.4), from a large population-based cohort of twins.

The scientists found that higher serum vitamin D concentrations were significantly associated with longer telomeres, and that the difference in telomere length between the highest and lowest levels of vitamin D was highly significant and equivalent to five years of aging. The authors concluded that higher vitamin D levels, easily modifiable through nutritional supplementation, were associated with longer telomere length.[34]

Chelation

In the skin of albino hairless mice (Skh:HR-I) there is a basal level of non-heme iron. Chronic exposure of mice to sub-erythemal doses of ultraviolet (UV) B radiation results in an increased skin level of non-heme iron. The iron increase may be the result of a UVB radiation-induced increase in vascular permeability, which we measured in vivo with the dye marker Evans Blue. We also observed greater non-heme iron in sun-exposed vs non-exposed body sites of human skin, suggesting that similar events occur in man.

Iron may have a role in skin photodamage by participating in formation of reactive oxygen species. These species have been implicated in skin photodamage. It is known that iron can contribute to oxygen radical production by acting catalytically in the formation of species such as hydroxyl radical. While the basal level of skin iron may be available for catalysis, the elevated iron content of UV-exposed skin increases the potential for iron-catalyzed radical production.

Topical application of certain iron chelators to Skh albino hairless mice dramatically delayed the onset of UVB radiation-induced skin photodamage. Non-chelating analogs provided no significant protection.[35]

Increased total fat mass and visceral fat may account in part for age-associated decrease in hepatic insulin action. Body fat and its distribution are major determinants of age-associated hepatic insulin resistance.[36]

Lower brain glucose metabolism is present before the onset of clinically measurable cognitive decline in two groups of people at risk of Alzheimer's disease—carriers of apolipoprotein E4, and in those with a maternal family history of AD. Supported by emerging evidence from in vitro and animal studies, these reports suggest that brain hypometabolism may precede and therefore contribute to the neuropathologic cascade leading to cognitive decline in AD. The reason brain hypometabolism develops is unclear but may include defects in brain glucose transport, disrupted glycolysis, and/or impaired mitochondrial function. Methodologic issues presently preclude knowing with certainty whether or not aging in the absence of cognitive impairment is necessarily associated with lower brain glucose metabolism. Nevertheless, aging appears to increase the risk of deteriorating systemic control of glucose utilization, which, in turn, may increase the risk of declining brain glucose uptake, at least in some brain regions. A contributing role of deteriorating glucose availability to or metabolism by the brain in AD does not exclude the opposite effect, i.e., that neurodegenerative processes in AD further decrease brain glucose metabolism because of reduced synaptic functionality and hence reduced energy needs, thereby completing a vicious cycle. Strategies to reduce the risk of AD by breaking this cycle should aim to (1) improve insulin sensitivity by improving systemic glucose utilization, or (2) bypass deteriorating brain glucose metabolism using approaches that safely induce mild, sustainable ketonemia.[37]

[1] Mark A. Smith, et al, *Increased Iron and Free Radical Generation in Preclinical Alzheimer Disease and Mild Cognitive Impairment J Alzheimers Dis.* 2010 January; 19(1): 363-372.

[2] S. G, Sukkar, G. Bounous, *The Role of Whey Protein in Antioxidant Defense, Rivista Italiana di Nutrizione Parenterale ed Enterale*, Anno 22 n. 4, pp. 193-200 (2004)

[3] David W. Killilea, Hani Atamna, Chares Liao, Bruce N. Ames. Antioxidants & Redox Signaling. October 2003, 5(5): 507-516

[4] Kyle E. Brown, et al, *Increased hepatic-telomerase activity in a rat model of iron overload: a role for, altered thiol redox state?, Free Radic Biol Med.* 2007 Jan. 15; 42(2): 228-235.

[5] Qiong Liu, at al. *Effects of trace elements on the telomere lengths of hepatocytes L-02 and hepatoma cells SMMC-7721, Biological Trace Element Research*, Volume 100, Number 3, 21-227

[6] Naslund J, et al, *Correlation between elevated levels, of amyloid beta-peptide in the brain and cognitive decline, JAMA.* 2000 Mar. 22-29; 283(12):1571-7

[7] Paul S. Aisen, *Alzheimer's Disease Therapeutic Research: the Path Forward, Alzheimer's Research & Therapy,* 2009, 1; 2

[8] UCLA Newsroom, http://www.eurekalert.org/pub_releases/2009-09/uoc-rad092209.php

[9] Debette, S., et. al. (2010). *Visceral fat is associated with lower brain volume in healthy middle-aged adults* Ann. Neurol. DOI: 10.1002/ana.22062

[10] Ho, A., et, at, (2010). *A commonly carried allele of the obesity-related FTO gene is associated with reduced brain volume in the healthy elderly.* Proc. Nat, Aced. Sci. 107: 8404-8409.

[11] A. David Smith, et al, *Homocysteine-Lowering by B Vitamins Slows the Rate of Accelerated Brain Atrophy in Mild Cognitive Impairment: A Randomized Controlled Trial,* PLoS ONE 5(9): e12244. doi: 10.1371/journal.pone.0012244

[12] Green, K., *Journal of Neuroscience,* Apr. 18, 2007; vol 27.

[13] Richard Wurtman, *Brain Research,* IANA 2006 Symposium II on Nutrition and Alzheimer's Disease/Cognitive Decline

[14] Bruce Cole, Qui-Lan Ma, Bruce Toeter, Oliver J. Ubede, Takashi Morihara, Dilsher Dhoot, Michael D. Nyby, Michael L. Tuck and Sally A. Frautschy, *Journal of Neuroscience,* 2007

[15] *Reporter,* Oct. 19, 2007, Vanderbilt University Medical Center

[16] Lauren C Costantini, et al *Hypometabolism as a therapeutic target in Alzheimer's disease,* Proceedings of the $8^{th}$ International Conference on Alzheimer's Disease, Drug Discovery, October 2007

[17] M'hamed Bentourkia, et al, *PET study of $^{11}C$ acetoacetate kinetics in rat brain during dietary treatments affecting ketosis,* Am J Physiol Endocrinol Metab 296: E796-E801, 2009

[18] Lisa Mosconi, Alberto Pupi, and Many J. De Leon, Brain Glucose Hypometabolism and Oxidative Stress in Preclinical Alzheimers Disease, Ann NY Acad Sci. 2008 December; 1147: 180-195.

[19] Nutritional Neuroscience (2010 June; 13(3):116-22

[20] Krikorian R, et al, *Improved cognitive-cerebral function in older adults with chromium supplementation.* http://www.ncbi.nlm.nih.gov/pubmed/20423560

[21] Benedict C, et al, *Intranasal insulin improves memory in humans,* Psychoneuroendocrinology. 2004 November; 29(10):1326-34.

[22] Sahin K, at al, *The Effects of Chromium Complex and Level on Glucose Metabolism and Memory Acquisition in Rats Fed High-Fat Diet.* Biol Trace Elem Res. 2010 Dec. 1.

[23] Smith M A, et al, *Increased iron and free radical generation in preclinical Alzheimer disease and mild cognitive impairment.* J Alzheimers Dis. 2010 January; 19(1): 363-72.

[24] Mark A. Smith, et al, *Iron accumulation in Alzheimer disease is a source of redox-generated free radicals,* PNAS Sep. 2, 1997 vol. 94 no. 18 9866-9868

[25] David W. Killilea, Hani Atamna, Charles Liao, Bruce N. Ames. *Iron Accumulation During Cellular Senescence in Human Fibroblasts In Vitro, Antioxidants & Redox Signaling.* October 2003, 5(5): 507-516;

[26] James Stankiewicz, et al, *Iron in Chronic Brain Disorders: Imaging and Neurotherapeutic Implications, Neurotherapeutics.* 2007 July; 4(3): 371-386.

[27] PREM PONKA, *Hereditary Causes of Disturbed Iron Homeostasis in the Central Nervous System.* Annals of the New York Academy of Sciences, Volume 1012, Redox-Active Metals in Neurological Disorders pages 267-281, March 2004

[28] M Morris, D Evans, J Bienias, P Scherr, C Tangney, L Hebert, D Bennett, R Wilson, and N Aggarwal *Dietary niacin and the risk of incident Alzheimer's disease and of cognitive decline* J Neurol Neurosurg Psychiatry. 2004 August; 75(8): 1093-1099.

[29] Luckhaus C, et al, *Blood biomarkers of osteoporosis in mild cognitive impairment and Alzheimer's disease.* J Neural Transm. 2009 July; 116(7):905-11

[30] Masoumi A, et al, $1alpha,25$-dihydroxyvitamin D3 interacts with curcuminoids to stimulate amyloid-beta clearance by macrophages of Alzheimer's disease patients. J Alzheimers Dis. 2009; 17(3):703-17

[31] Buell J S, et al 25-*Hydroxyvitamin D, dementia, and cerebrovascular pathology in elders receiving home services.* Neurology. 2010 Jan. 5; 74(1):18-26.

[32] Oudshoom C, et al, *Higher serum vitamin D3 levels are associated with better cognitive test performance in patients with Alzheimer's disease,* Dement Geriatr Cogn Disord. 2008; 25(6):539-43. Epub 2008 May 26.

[33] Wilkins C H, et al, *Vitamin D deficiency is associated with low mood and worse cognitive performance in older adults.* Am J Geriatr Psychiatry. 2006 December; 14(12): 1032-40.

[34] Richard J B, Valdes A M, at al. *Higher serum vitamin D concentrations are associated with longer leukocyte telomere length in women.* Am J Clin Nutr. 2007 November; 86(5):1420-5

[35] Donald L. Bissett, Ranjit Chatterjee, Daniel P. Hannon *Chronic Ultraviolet Radiation-Induced Increase in Skin Iron and the Photoprotective Effect of Topically Applied Iron Chelators.* Photochemistry and Photobiology Volume 54, Issue 2, pages 215-223, August 1991

[36] Gaurav Gupta, et al, Ability of insulin to modulate hepatic glucose production in aging rats is impaired by fat accumulation, Am J Physiol Endocrinol Metab 278: E985-E991, 2000

[37] Cunnane S, at al, *Brain fuel metabolism, aging, and Alzheimer's disease,* Nutrition. 2010 Oct. 28.

I claim:

1. A method for treating a patient with Alzheimer's disease, comprising:
    topically administering to the patient an aqueous solution containing chromium (III) at a concentration of 10 milligram per ounce of the solution for removing excessive iron from the cells in brain and reducing oxidative stress, and magnesium sulfate at a concentration of 1 gram per ounce of the solution to facilitate skin absorption of the chromium through skin; and subsequently
    engaging physical activity designed to elevate a pulse rate of the patient to at least 60% of maximum for about 10 to 30 minutes.

2. The method of claim 1 wherein the solution further comprises cyanocobalamin for further enhancing the absorption of the chromium (III) through skin.

* * * * *